United States Patent
Stein et al.

(10) Patent No.: US 8,939,030 B2
(45) Date of Patent: Jan. 27, 2015

(54) EDGE-DETECT RECEIVER FOR ORTHOPEDIC PARAMETER SENSING

(71) Applicants: Marc Stein, Chandler, AZ (US); Andrew Kelly, Scottsdale, AZ (US)

(72) Inventors: Marc Stein, Chandler, AZ (US); Andrew Kelly, Scottsdale, AZ (US)

(73) Assignee: Orthosensor Inc, Dania Beach, FL (US)

( * ) Notice: Subject to any disclaimer, the term of this patent is extended or adjusted under 35 U.S.C. 154(b) by 53 days.

(21) Appl. No.: 13/902,704

(22) Filed: May 24, 2013

(65) Prior Publication Data
US 2013/0261450 A1 Oct. 3, 2013

Related U.S. Application Data

(63) Continuation of application No. 12/826,085, filed on Jun. 29, 2010, now Pat. No. 8,490,488.

(51) Int. Cl.
| | |
|---|---|
| G01N 29/44 | (2006.01) |
| G01N 3/32 | (2006.01) |
| A61B 5/00 | (2006.01) |

(52) U.S. Cl.
CPC .............. *A61B 5/7239* (2013.01); *G01N 29/44* (2013.01); *A61B 5/6846* (2013.01); *A61B 5/4528* (2013.01); *A61B 5/0031* (2013.01); *A61B 5/4509* (2013.01); *A61B 5/4585* (2013.01); *A61B 5/7225* (2013.01)
USPC .............................. 73/584; 600/437; 600/587

(58) Field of Classification Search
USPC .................................................. 73/584, 658
See application file for complete search history.

(56) References Cited

U.S. PATENT DOCUMENTS

| | | | | |
|---|---|---|---|---|
| 4,066,082 | A | | 1/1978 | Arcan et al. |
| 4,480,485 | A | * | 11/1984 | Bradshaw et al. ......... 73/861.28 |
| 4,899,761 | A | | 2/1990 | Brown et al. |
| 4,920,279 | A | * | 4/1990 | Charlet et al. ................ 327/306 |
| 4,986,281 | A | * | 1/1991 | Preves et al. .................. 600/595 |
| 5,339,691 | A | * | 8/1994 | Smith et al. ...................... 73/597 |
| 5,456,724 | A | | 10/1995 | Yen et al. |
| 5,470,354 | A | | 11/1995 | Hershberger et al. |
| 5,521,550 | A | * | 5/1996 | Doak ............................. 330/10 |
| 5,733,292 | A | | 3/1998 | Gustilo et al. |
| 6,517,487 | B1 | * | 2/2003 | Mazess et al. ................ 600/449 |
| 6,583,630 | B2 | * | 6/2003 | Mendes et al. ................ 324/652 |
| 6,714,763 | B2 | * | 3/2004 | Hamel et al. .................... 73/786 |
| 6,739,068 | B1 | | 5/2004 | Rinner |
| 6,796,988 | B2 | | 9/2004 | Melkent et al. |
| 6,856,141 | B2 | * | 2/2005 | Ariav ............................ 324/639 |
| 7,080,554 | B2 | * | 7/2006 | Ariav et al. ..................... 73/579 |
| 7,097,662 | B2 | * | 8/2006 | Evans et al. ................ 623/18.11 |
| 7,153,281 | B2 | | 12/2006 | Holmes |

(Continued)

*Primary Examiner* — Randy W Gibson
*Assistant Examiner* — Natalie Huls

(57) ABSTRACT

A sensor system uses positive closed-loop feedback to provide energy waves into a medium. The medium can be coupled to the muscular-skeletal system or be part of the muscular-skeletal system. A sensor comprises one or more transducers, an edge detect circuit or a reflecting surface. A parameter is applied to the medium and the parameter affects the medium. A transducer receives an energy wave that has traversed the medium and generates an energy wave signal. The edge-detect receiver receives the energy wave signal signal from the transducer and generates a pulse upon sensing a leading edge corresponding to a wave front of the energy wave. The edge-detect receiver comprises a preamplifier, a differentiator, a digital pulse circuit, and a deblank circuit. The transit time, phase, or frequency is measured of the propagating energy waves and correlated to the parameter being measured.

20 Claims, 5 Drawing Sheets

(56) References Cited

U.S. PATENT DOCUMENTS

| | | |
|---|---|---|
| 7,195,645 B2 * | 3/2007 | Disilvestro et al. ........ 623/18.11 |
| 7,283,867 B2 | 10/2007 | Strother et al. |
| 7,384,403 B2 | 6/2008 | Sherman |
| 7,412,897 B2 | 8/2008 | Crottet et al. |
| 7,442,196 B2 | 10/2008 | Fisher et al. |
| 7,559,951 B2 | 7/2009 | DiSilvestro et al. |
| 7,575,602 B2 | 8/2009 | Amirouche et al. |
| 7,601,120 B2 * | 10/2009 | Moilanen et al. ............ 600/438 |
| 7,615,055 B2 | 11/2009 | DiSilvestro |
| 7,632,283 B2 | 12/2009 | Heldreth |
| 7,854,701 B2 * | 12/2010 | Stergiopoulos et al. ...... 600/442 |
| 8,202,219 B2 * | 6/2012 | Luo et al. ...................... 600/438 |
| 8,421,479 B2 * | 4/2013 | Stein ............................. 324/642 |
| 8,427,176 B2 * | 4/2013 | Stein ............................. 324/639 |
| 8,490,488 B2 * | 7/2013 | Stein et al. ...................... 73/584 |
| 8,761,859 B2 * | 6/2014 | Roche ........................... 600/407 |
| 2002/0049394 A1 | 4/2002 | Roy et al. |
| 2003/0036764 A1 | 2/2003 | Hamada |
| 2003/0069644 A1 | 4/2003 | Kovacevic et al. |
| 2003/0187351 A1 | 10/2003 | Franck et al. |
| 2004/0064073 A1 | 4/2004 | Heldreth |
| 2004/0152970 A1 | 8/2004 | Hunter et al. |
| 2005/0010299 A1 | 1/2005 | Disilvestro |
| 2005/0010302 A1 | 1/2005 | Dietz et al. |
| 2005/0234555 A1 | 10/2005 | Sutton |
| 2005/0273170 A1 | 12/2005 | Navarro et al. |
| 2007/0129776 A1 | 6/2007 | Robins et al. |
| 2007/0233267 A1 | 10/2007 | Amirouche et al. |
| 2008/0082118 A1 | 4/2008 | Edidin et al. |
| 2008/0228195 A1 | 9/2008 | Von Jako et al. |

* cited by examiner

700

EDGE-DETECT RECEIVER FOR ORTHOPEDIC PARAMETER SENSING

CROSS-REFERENCE TO RELATED APPLICATIONS

This application is a continuation of U.S. patent application Ser. No. 12/826,085 filed Jun. 29, 2010 claiming priority benefit of U.S. Provisional Patent Application No. 61/221,923 filed on Jun. 30, 2009, the entire contents of which are hereby incorporated by reference. This application further claims the priority benefit of U.S. provisional patent application Nos. 61/221,761, 61/221,767, 61/221,779, 61/221,788, 61/221,793, 61/221,801, 61/221,808, 61/221,817, 61/221,867, 61/221,874, 61/221,879, 61/221,881, 61/221,886, 61/221,889, 61/221,894, 61/221,901, 61/221,909, 61/221,916, and 61/221,929 all filed 30 Jun. 2009. The disclosures of which are incorporated herein by reference in its entirety.

FIELD

The present invention pertains generally to measurement of physical parameters, and particularly to, but not exclusively, to circuitry for detecting specific features of the energy waves or pulses.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance.

BRIEF DESCRIPTIONS OF THE DRAWINGS

Various features of the system are set forth with particularity in the appended claims. The embodiments herein, can be understood by reference to the following description, taken in conjunction with the accompanying drawings, in which:

DETAILED DESCRIPTION OF EXEMPLARY EMBODIMENTS

Figure 1:
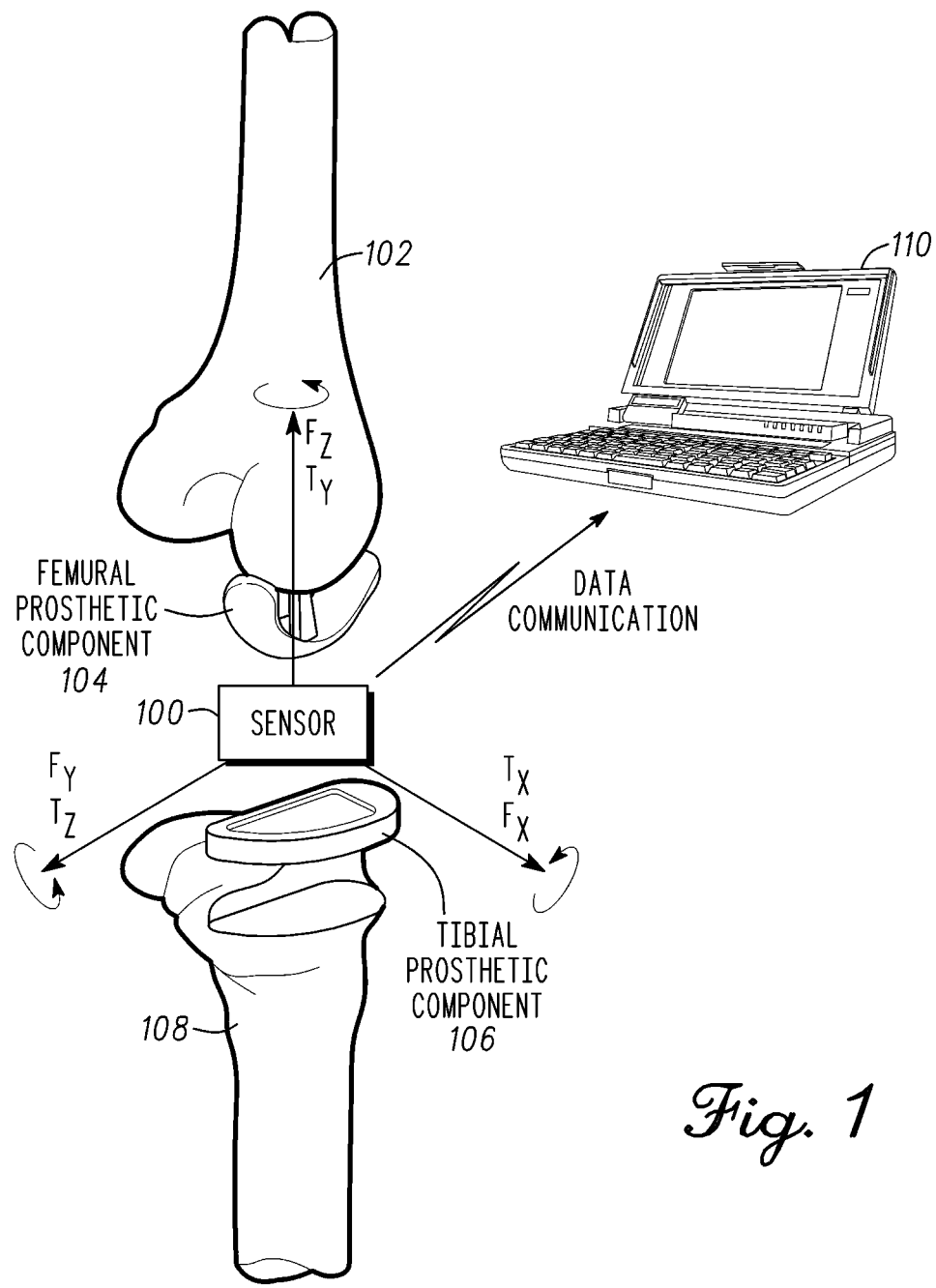
FIG. 1 is an illustration of a sensor placed in contact between a femur and a tibia for measuring a parameter in accordance with an exemplary embodiment.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate. For example specific computer code may not be listed for achieving each of the steps discussed, however one of ordinary skill would be able, without undo experimentation, to write such code given the enabling disclosure herein. Such code is intended to fall within the scope of at least one exemplary embodiment.

Additionally, the sizes of structures used in exemplary embodiments are not limited by any discussion herein (e.g., the sizes of structures can be macro (centimeter, meter, and larger sizes), micro (micrometer), and nanometer size and smaller).

Notice that similar reference numerals and letters refer to similar items in the following figures, and thus once an item is defined in one figure, it may not be discussed or further defined in the following figures.

FIG. 1 is an illustration of a sensor 100 placed in contact between a femur 102 and a tibia 108 for measuring a parameter in accordance with an exemplary embodiment. In general, a sensor 100 is placed in contact with or in proximity to the muscular-skeletal system to measure a parameter. In a non-limiting example, sensor 100 is used to measure a parameter of a muscular-skeletal system during a procedure such as an installation of an artificial joint. Embodiments of sensor 100 are broadly directed to measurement of physical parameters, and more particularly, to evaluating changes in the transit time of a pulsed energy wave propagating through a medium. In-situ measurements during orthopedic joint implant surgery would be of substantial benefit to verify an implant is in balance and under appropriate loading or tension. In one embodiment, the instrument is similar to and operates familiarly with other instruments currently used by surgeons. This will increase acceptance and reduce the adoption cycle for a new technology. The measurements will allow the surgeon to ensure that the implanted components are installed within predetermined ranges that maximize the working life of the joint prosthesis and reduce costly revisions. Providing quantitative measurement and assessment of the procedure using real-time data will produce results that are more consistent. A further issue is that there is little or no implant data generated from the implant surgery, post-operatively, and long term. Sensor 100 can provide implant status data to the orthopedic manufacturers and surgeons. Moreover, data generated by direct measurement of the implanted joint itself would greatly improve the knowledge of implanted joint operation and joint wear thereby leading to improved design and materials.

In at least one exemplary embodiment, an energy pulse is directed within one or more waveguides in sensor 100 by way of pulse mode operations and pulse shaping. The waveguide is a conduit that directs the energy pulse in a predetermined direction. The energy pulse is typically confined within the waveguide. In one embodiment, the waveguide comprises a polymer material. For example, urethane or polyethylene are polymers suitable for forming a waveguide. The polymer waveguide can be compressed and has little or no hysteresis in the system. Alternatively, the energy pulse can be directed through the muscular-skeletal system. In one embodiment, the energy pulse is directed through bone of the muscular-skeletal system to measure bone density. A transit time of an energy pulse is related to the material properties of a medium through which it traverses. This relationship is used to generate accurate measurements of parameters such as distance, weight, strain, pressure, wear, vibration, viscosity, and density to name but a few.

Sensor 100 can be size constrained by form factor requirements of fitting within a region the muscular-skeletal system or a component such as a tool, equipment, or artificial joint. In a non-limiting example, sensor 100 is used to measure load and balance of an installed artificial knee joint. A knee prosthesis comprises a femoral prosthetic component 104, an insert, and a tibial prosthetic component 106. A distal end of femur 102 is prepared and receives femoral prosthetic component 104. Femoral prosthetic component 104 typically has two condyle surfaces that mimic a natural femur. As shown, femoral prosthetic component 104 has single condyle surface being coupled to femur 100. Femoral prosthetic component 104 is typically made of a metal or metal alloy.

A proximal end of tibia 108 is prepared to receive tibial prosthetic component 106. Tibial prosthetic component 106 is a support structure that is fastened to the proximal end of the tibia and is usually made of a metal or metal alloy. The tibial prosthetic component 106 also retains the insert in a fixed position with respect to tibia 108. The insert is fitted between femoral prosthetic component 104 and tibial prosthetic component 106. The insert has at least one bearing surface that is in contact with at least condyle surface of femoral prosthetic component 104. The condyle surface can move in relation to the bearing surface of the insert such that the lower leg can rotate under load. The insert is typically made of a high wear plastic material that minimizes friction.

In a knee joint replacement process, the surgeon affixes femoral prosthetic component 104 to the femur 102 and tibial prosthetic component 106 to tibia 108. The tibial prosthetic component 106 can include a tray or plate affixed to the planarized proximal end of the tibia 108. Sensor 100 is placed between a condyle surface of femoral prosthetic component 104 and a major surface of tibial prosthetic component 106. The condyle surface contacts a major surface of sensor 100. The major surface of sensor 100 approximates a surface of the insert. Tibial prosthetic component 106 can include a cavity or tray on the major surface that receives and retains sensor 100 during a measurement process. Tibial prosthetic component 106 and sensor 100 has a combined thickness that represents a combined thickness of tibial prosthetic component 106 and a final (or chronic) insert of the knee joint.

In one embodiment, two sensors 100 are fitted into two separate cavities, the cavities are within a trial insert (that may also be referred to as the tibial insert, rather than the tibial component itself) that is held in position by tibial component 106. One or two sensors 100 may be inserted between femoral prosthetic component 104 and tibial prosthetic component 106. Each sensor is independent and each measures a respective condyle of femur 102. Separate sensors also accommodate a situation where a single condyle is repaired and only a single sensor is used. Alternatively, the electronics can be shared between two sensors to lower cost and complexity of the system. The shared electronics can multiplex between each sensor module to take measurements when appropriate. Measurements taken by sensor 100 aid the surgeon in modifying the absolute loading on each condyle and the balance between condyles. Although shown for a knee implant, sensor 100 can be used to measure other orthopedic joints such as the spine, hip, shoulder, elbow, ankle, wrist, interphalangeal joint, metatarsophalangeal joint, metacarpophalangeal joints, and others. Alternatively, sensor 100 can also be adapted to orthopedic tools to provide measurements.

The prosthesis incorporating sensor 100 emulates the function of a natural knee joint. Sensor 100 can measure loads or other parameters at various points throughout the range of motion. Data from sensor 100 is transmitted to a receiving station 110 via wired or wireless communications. In a first embodiment, sensor 100 is a disposable system. Sensor 100 can be disposed of after using sensor 100 to optimally fit the joint implant. Sensor 100 is a low cost disposable system that reduces capital costs, operating costs, facilitates rapid adoption of quantitative measurement, and initiates evidentiary based orthopedic medicine. In a second embodiment, a methodology can be put in place to clean and sterilize sensor 100 for reuse. In a third embodiment, sensor 100 can be incorporated in a tool instead of being a component of the replacement joint. The tool can be disposable or be cleaned and sterilized for reuse. In a fourth embodiment, sensor 100 can be a permanent component of the replacement joint. Sensor 100 can be used to provide both short term and long term post-operative data on the implanted joint. In a fifth embodiment, sensor 100 can be coupled to the muscular-skeletal system. In all of the embodiments, receiving station 110 can include data processing, storage, or display, or combination thereof and provide real time graphical representation of the level and distribution of the load. Receiving station 110 can record and provide accounting information of sensor 100 to an appropriate authority.

In an intra-operative example, sensor 100 can measure forces (Fx, Fy, Fz) with corresponding locations and torques (e.g. Tx, Ty, and Tz) on the femoral prosthetic component 104 and the tibial prosthetic component 106. The measured force and torque data is transmitted to receiving station 110 to provide real-time visualization for assisting the surgeon in identifying any adjustments needed to achieve optimal joint pressure and balancing. The data has substantial value in determining ranges of load and alignment tolerances required to minimize rework and maximize patient function and longevity of the joint.

As mentioned previously, sensor 100 can be used for other joint surgeries; it is not limited to knee replacement implant or implants. Moreover, sensor 100 is not limited to trial measurements. Sensor 100 can be incorporated into the final joint system to provide data post-operatively to determine if the implanted joint is functioning correctly. Early determination of a problem using sensor 100 can reduce catastrophic failure of the joint by bringing awareness to a problem that the patient cannot detect. The problem can often be rectified with a minimal invasive procedure at lower cost and stress to the patient. Similarly, longer term monitoring of the joint can determine wear or misalignment that if detected early can be adjusted for optimal life or replacement of a wear surface with minimal surgery thereby extending the life of the implant. In general, sensor 100 can be shaped such that it can be placed or engaged or affixed to or within load bearing surfaces used in many orthopedic applications (or used in any orthopedic application) related to the musculoskeletal system, joints, and tools associated therewith. Sensor 100 can provide information on a combination of one or more performance parameters of interest such as wear, stress, kinematics, kinetics, fixation strength, ligament balance, anatomical fit and balance.

Figure 2:
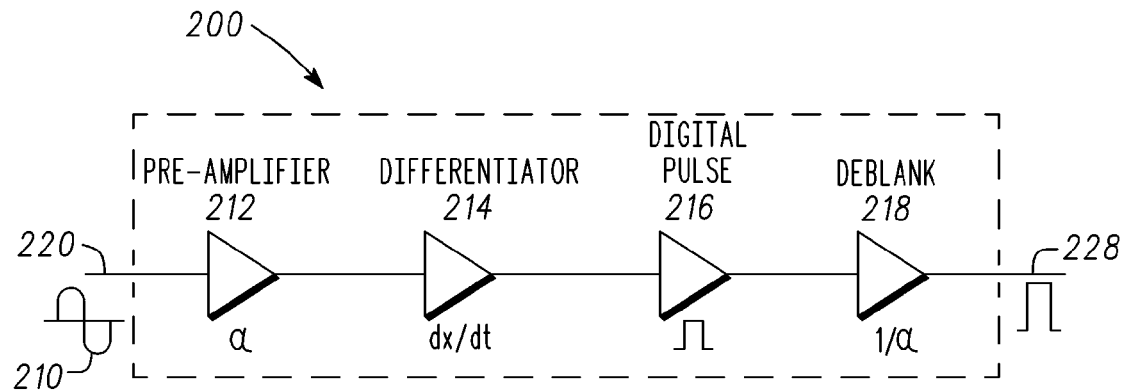
FIG. 2 illustrates a block diagram of an edge-detect receiver circuit in accordance with an exemplary embodiment.

FIG. 2 illustrates a block diagram of an edge-detect receiver circuit 200 in accordance with an exemplary embodiment. In a first embodiment, edge-detect receiver 200 is provided to detect wave fronts of energy waves. This enables capturing of parameters including, but not limited to, transit time, phase, or frequency of the energy waves. Circuitry of the integrated edge-detect receiver 200 provides rapid on-set detection and quickly responds to the arrival of an energy wave. It reliably triggers thereafter a digital output pulse at a same point on the initial wave front of each captured energy wave or pulsed energy wave. The digital pulse can be optimally configured to output with minimal and constant delay. The edge-detect receiver 200 can isolate and precisely detect the specified point on the initial energy wave or the wave front in the presence of interference and distortion signals thereby overcoming problems commonly associated with detecting one of multiply generated complex signals in energy propagating mediums. The edge-detect receiver 200 performs these functions accurately over a wide range of amplitudes including very low level energy waves and pulses.

In a second embodiment, the edge-detect receiver 200 is incorporated within a propagation tuned oscillator (PTO) to maintain positive closed-loop feedback when operating in a continuous wave, pulse, or pulse-echo mode. The edge-detect receiver 200 can be integrated with other circuitry of the PTO by multiplexing input and output circuitry to achieve ultra low-power and small compact size. Integration of the circuitry of the PTO with the edge-detect receiver provides the benefit of increasing sensitivity to low-level signals.

The block diagram illustrates one embodiment of a low power edge-detect receiver circuit 200 with superior performance at low signal levels. The edge-detect receiver 200 comprises a preamplifier 212, a differentiator 214, a digital pulse circuit 216 and a deblank circuit 218. The edge-detect receiver circuit 200 can be implemented in discrete analog components, digital components or combination thereof. In one embodiment, edge-detect receiver 200 is integrated into an ASIC as part of a sensor system described hereinbelow. The edge-detect receiver circuit 200 practices measurement methods that detect energy pulses or pulsed energy waves at specified locations and under specified conditions to enable capturing parameters including, but not limited to, transit time, phase, frequency, or amplitude of energy waves. A brief description of the method of operation is as follows. In a non-limiting example, a pre-amplifier triggers a comparator circuit responsive to small changes in the slope of an input signal. The comparator and other edge-detect circuitry responds rapidly with minimum delay. Detection of small changes in the input signal assures rapid detection of the arrival of energy waves. The minimum phase design reduces extraneous delay thereby introducing less variation into the measurement of the transit time, phase, frequency, or amplitude of the incoming energy waves.

An input 220 of edge-detect receiver 200 is coupled to pre-amplifier 212. As an example, the incoming wave 210 to the edge-detect receiver circuit 200 can be received from an electrical connection, antenna, or transducer. The incoming wave 210 is amplified by pre-amplifier 212, which assures adequate sensitivity to small signals. Differentiator circuitry 214 monitors the output of pre-amplifier 212 and triggers digital pulse circuitry 216 whenever a signal change corresponding to an energy wave is detected. For example, a signal change that identifies the energy wave is the initial wave front or the leading edge of the energy wave. In one arrangement, differentiator 214 detects current flow, and more specifically changes in the slope of the energy wave 210 by detecting small changes in current flow instead of measuring changes in voltage level to achieve rapid detection of slope. Alternatively, differentiator 214 can be implemented to trigger on changes in voltage. Together, preamplifier 212 and differentiator 214 monitor the quiescent input currents for the arrival of wave front of energy wave(s) 210. Preamplifier 212 and differentiator 214 detect the arrival of low level pulses of energy waves as well as larger pulse of energy waves. This detection methodology achieves superior performance for very low level signals. Differentiator circuitry 214 triggers digital pulse circuitry 216 whenever current flow driven by the initial signal ramp of the incoming wave 210 is detected. The digital pulse is coupled to deblank circuit 218 that desensitizes pre-amplifier 212. For example, the desensitization of pre-amplifier 212 can comprise a reduction in gain, decoupling of input 220 from energy wave 210, or changing the frequency response. The deblank circuit 218 also disregards voltage or current levels for a specified or predetermined duration of time to effectively skip over the interference sections or distorted portions of the energy wave 210. In general, energy wave 210 can comprise more than one change in slope and is typically a damped wave form. Additional signals or waves of the pulsed energy wave on the input 220 of pre-amplifier 212 are not processed during the preset blanking period. In this example, the digital output pulse 228 can then be coupled to signal processing circuitry as explained hereinbelow.

In one embodiment, the electronic components are operatively coupled as blocks within an integrated circuit. As will be shown ahead, this integration arrangement performs its specific functions efficiently with a minimum number of components. This is because the circuit components are partitioned between structures within an integrated circuit and discrete components, as well as innovative partitioning of analog and digital functions, to achieve the required performance with a minimum number of components and minimum power consumption.

Figure 3:
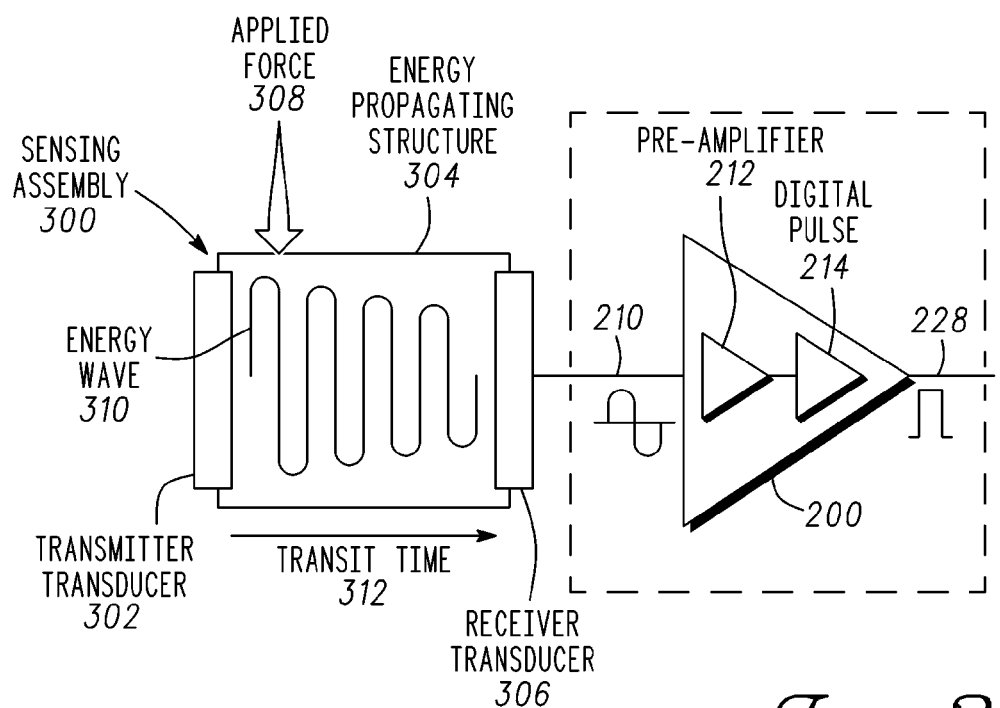
FIG. 3 illustrates a block diagram of the edge-detect receiver circuit coupled to a sensing assembly in accordance with an exemplary embodiment.

FIG. 3 illustrates a block diagram of the edge-detect receiver circuit 100 coupled to a sensing assembly 300. The pre-amplifier 212 and the digital pulse circuit 214 are shown for reference and discussion. The sensing assembly 300 comprises a transmitter transducer 302, an energy propagating medium 304, and a receiver transducer 306. The transmitter transducer 302 is coupled to propagating medium 304 at a first location. The receiver transducer is coupled to energy propagating medium 304 at a second location. As will be explained ahead in further detail, the sensing assembly 300 in one embodiment is part of a sensory device that assess loading, in particular, the externally applied forces 308 on the sensing assembly 300. A transducer driver circuit (not shown) drives the transmitter transducer 302 of the sensing assembly 300 to produce energy waves 310 that are directed into the energy propagating medium 304. In the non-limiting example, changes in the energy propagating medium 304 due to the externally applied forces 308 change the frequency, phase, and transit time 312 of energy waves 310 propagating from the first location to the second location of energy propagating medium 304. The integrated edge-detect receiver circuit 200 is coupled to the receiver transducer 306 to detect edges of the reproduced energy wave 210 and trigger the digital pulse 228. In general, the timing of the digital pulse 228 conveys the parameters of interest (e.g., distance, force weight, strain, pressure, wear, vibration, viscosity, density, direction, displacement, etc.) related to the change in energy propagating structure 304 due to an external parameter. For example, sensing assembly 300 placed in a knee joint as described hereinabove.

Measurement methods that rely on the propagation of energy pulses require the detection of energy pulses at specified locations or under specified conditions to enable capturing parameters including, but not limited to, transit time, phase, frequency, or amplitude of the energy pulses. Measurement methods that rely on such propagation of energy waves 310 or pulses of energy waves are required to achieve highly accurate and controlled detection of energy waves or pulses. Moreover, pulses of energy waves may contain multiple energy waves with complex waveforms therein leading to potential ambiguity of detection. In particular, directing energy waves 310 into the energy propagating structure 304 can generate interference patterns caused by nulls and resonances of the waveguide, as well as characteristics of the generated energy wave 310. These interference patterns can generate multiply excited waveforms that result in distortion of the edges of the original energy wave. To reliably detect the arrival of a pulse of energy waves, the edge-detect receiver 200 only responds to the leading edge of the first energy wave within each pulse. This is achieved in part by blanking the edge-detect circuitry 200 for the duration of each energy pulse. As an example, the deblank circuit 218 disregards voltage or current levels for a specified duration of time to effectively skip over the interference sections or distorted portions of the waveform.

There are a wide range of applications for compact measurement modules or devices having ultra low power circuitry that enables the design and construction of highly performing measurement modules or devices that can be tailored to fit a wide range of non-medical and medical applications. Applications for highly compact measurement modules or devices may include, but are not limited to, disposable modules or devices as well as reusable modules or devices and modules or devices for long term use. In addition to non-medical applications, examples of a wide range of potential medical applications may include, but are not limited to, implantable devices, modules within implantable devices, intra-operative implants or modules within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment.

Figure 4:
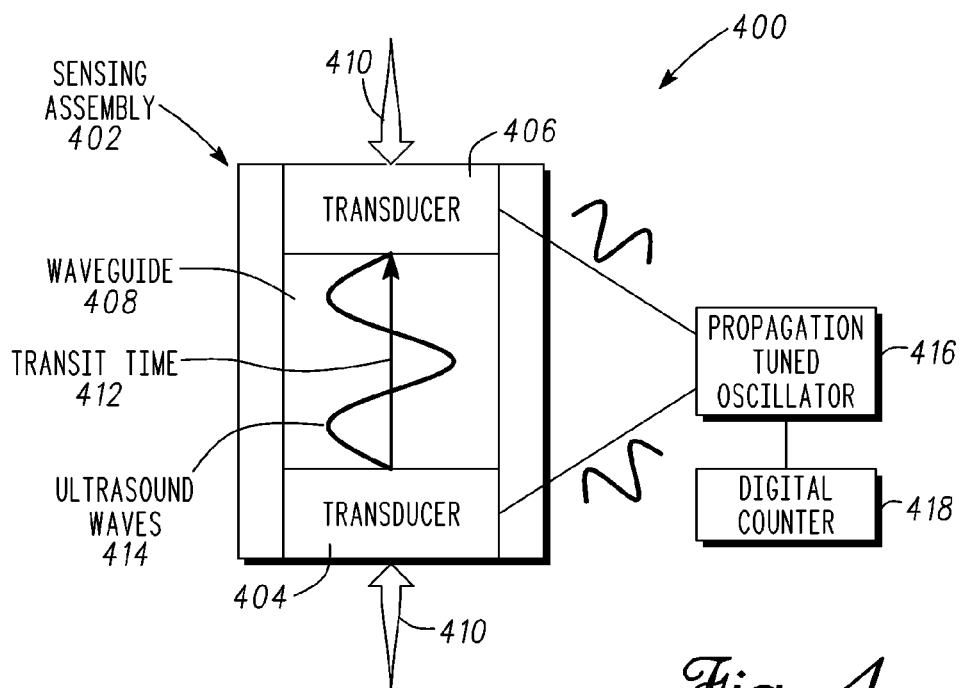
FIG. 4 is an exemplary propagation tuned oscillator (PTO) incorporating the edge-detect receiver circuit to maintain positive closed-loop feedback in accordance with one embodiment.

FIG. 4 is an exemplary propagation tuned oscillator (PTO) 400 incorporating the edge-detect receiver circuit 200 to maintain positive closed-loop feedback in accordance with one embodiment. The PTO is provided to maintain positive closed-loop feedback of energy waves in the energy propagating structures of the sensing assembly 402. A positive feedback closed-loop circuit causes the PTO to tune the resonant frequency of the energy waves in accordance with physical changes in the one or more energy propagating structures; hence the term, propagation tuned oscillator. The physical changes occur from an applied parameter to the propagating medium. For example, temperature changes or length changes are different parameters that can modify the propagating medium dimensionally. The length change can result from externally applied forces or pressure. In one embodiment, the physical changes in the energy propagating structures change in direct proportion to the external applied forces and can be precisely evaluated to measure the applied forces.

The sensing assembly 402 comprises a first transducer 404, a second transducer 406, and a waveguide 408. The waveguide 408 is an energy propagating structure or medium. Waveguide 408 contains and directs the energy wave. The sensing assembly 402 is affixed to load bearing or contacting surfaces 410. In one embodiment, external forces applied to the contacting surfaces 410 compress the waveguide 408 and change the length of the waveguide 408. This pushes the transducers 404 and 406 closer to together. This change in distance affects a transmit time 412 of energy waves 414 transmitted and received between transducers 404 and 406. The PTO 416 in response to these physical changes alters the oscillation frequency of the ultrasound waves 414 to achieve resonance.

Notably, changes in the waveguide 408 (energy propagating structure or structures) alter the propagation properties of the medium of propagation (e.g. transmit time 412). Due to the closed-loop operation shown, the PTO 416 changes the resonant frequency of the oscillator and accordingly the frequency of oscillation of the closed loop circuit. In one embodiment, the PTO 416 adjusts the oscillation frequency to be an integer number of waves. A digital counter 418 in conjunction with electronic components counts the number of waves to determine the corresponding change in the length of the waveguide 408. These changes in length change in direct proportion to the external force thus enabling the conversion of changes in parameter or parameters of interest into electrical signals.

The following is an example of the operation of sensing assembly 402, propagation tuned oscillator 416, and digital counter 418. In the example, the energy waves are acoustic waves at ultrasonic frequencies. The frequency of ultrasound waves 414 is controlled by propagation tuned oscillator 416. The ultrasound waves are emitted by ultrasound resonator or transducer 404 into a first location of waveguide 408. The emitted ultrasound waves by transducer 404 propagate through waveguide 408.

In the illustrated embodiment, a transducer 406 is coupled to waveguide 408 at a second location. Energy waves are emitted by transducer 404 into waveguide 408. Ultrasound waves 414 propagate to the second location and received by transducer 406. In one embodiment, transducer 406 outputs an electrical wave corresponding to ultrasound waves 414. In general, the transit time 412 of ultrasound waves 414 to propagate from the first location to the second location of waveguide 408 determines the period of oscillation of propagation tuned oscillator 416. Alternatively, transducer 404 can be both emit and receive energy waves. A reflecting surface at the second location can be used to direct the energy waves back to transducer 404 to be received. Transducer 404 toggles back and forth between the emitting and receiving modes.

Under quiescent conditions, the length of waveguide 408 does not change. Thus, the frequency of propagation tuned oscillator 416 remains constant. Changes in external forces or conditions 410 affect the propagation characteristics of waveguide 408 and alter transit time 412. In one embodiment, the number of wavelengths of ultrasound waves 414 is held constant by propagation tuned oscillator 416. Holding the number of wavelengths or energy waves constant at an integer number forces the frequency of oscillation of propagation tuned oscillator 416 to change. The resulting changes in frequency are captured with digital counter 418 that corresponds to external forces or conditions 410. In general, there is a known relationship between the parameter being applied to waveguide 408 and the length of waveguide 408. PTO 416 and digital counter 418 provides an accurate measurement of the length of waveguide 408. The known relationship between length and the parameter is then applied to the measurement to convert the measured length to the parameter measurement.

The closed loop measurement of the PTO enables high sensitivity and signal-to-noise ratio, as closed-loop time-based measurements are largely insensitive to most sources of error that may influence voltage or current driven sensing methods and devices. The resulting changes in the frequency of operation can be measured rapidly and with high resolution. This achieves the required measurement accuracy and precision thus capturing changes in the physical parameters of interest and enabling analysis of their dynamic and static behavior.

The level of accuracy and resolution achieved by the integration of energy transducers and an energy propagating structure or structures coupled with the electronic components of the propagation tuned oscillator enables the construction of, but is not limited to, compact ultra low power modules or devices for monitoring or measuring the parameters of interest. The flexibility to construct sensing modules or devices over a wide range of sizes enables sensing modules to be tailored to fit a wide range of applications such that the sensing module or device may be engaged with, or placed, attached, or affixed to, on, or within a body, instrument, appliance, vehicle, equipment, or other physical system and monitor or collect data on physical parameters of interest without disturbing the operation of the body, instrument, appliance, vehicle, equipment, or physical system.

Measurement methods that rely on the propagation of energy waves, or energy waves within energy pulses, may require the detection of a specific point of energy waves at specified locations, or under specified conditions, to enable capturing parameters including, but not limited to, transit time, phase, or frequency of the energy waves. Measurement of the changes in the physical length of individual ultrasound waveguides may be made in several modes. Each assemblage of one or two ultrasound resonators or transducers combined with an ultrasound waveguide may be controlled to operate in six different modes. This includes two wave shape modes: continuous wave or pulsed waves, and three propagation modes: reflectance, unidirectional, and bi-directional propagation of the ultrasound wave. The resolution of these measurements can be further enhanced by advanced processing of the measurement data to enable optimization of the trade-offs between measurement resolution versus length of the waveguide, frequency of the ultrasound waves, and the bandwidth of the sensing and data capture operations, thus achieving an optimal operating point for a sensing module or device.

Figure 5:
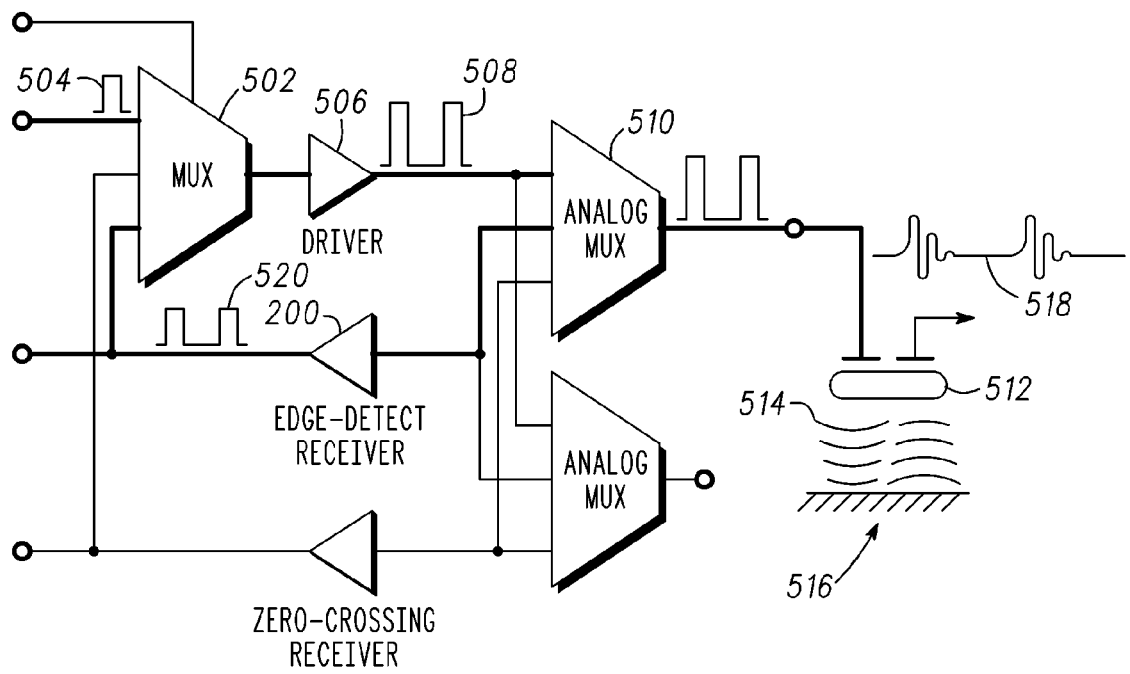
FIG. 5 is a sensor interface diagram incorporating the integrated edge-detect receiver circuit in a pulse-echo multiplexing arrangement for maintaining positive closed-loop feedback in accordance with one embodiment.

FIG. 5 is a sensor interface diagram incorporating the integrated edge-detect receiver circuit 200 in a pulse-echo multiplexing arrangement for maintaining positive closed-loop feedback in accordance with one embodiment. The positive closed-loop feedback is illustrated by the bold line path. Initially, multiplexer (mux) 502 receives as input a digital pulse 504, which is passed to the transducer driver 506 to produce the pulse sequence 508. Analog multiplexer (mux) 510 receives pulse sequence 508, which is passed to the transducer 512 to generate energy pulses 514. Energy pulses 514 are emitted into a first location of a medium and propagate through the medium. In the pulse-echo example, energy pulses 514 are reflected off a surface 516 at a second location of the medium, for example, the end of a waveguide or reflector, and echoed back to the transducer 512. The transducer 512 proceeds to then capture the reflected pulse echo. In pulsed echo mode, the transducer 512 performs as both a transmitter and a receiver. As disclosed above, transducer 512 toggles back and forth between emitting and receiving energy waves. Transducer 512 captures the reflected echo pulses, which are coupled to analog mux 510 and directed to the edge-detect receiver 200. The captured reflected echo pulses is indicated by electrical waves 518. Edge-detect receiver 200 locks on pulse edges corresponding to the wave front of a propagated energy wave to determine changes in phase and frequency of the energy pulses 514 responsive to an applied force, as previously explained. Among other parameters, it generates a pulse sequence 520 corresponding to the detected signal frequency. The pulse sequence 520 is coupled to mux 502 and directed to driver 506 to initiate one or more energy waves being emitted into the medium by transducer 512. Pulse 504 is decoupled from being provided to driver 506. Thus, a positive closed loop feedback is formed that repeatably emits energy waves into the medium until mux 502 prevents a signal from being provided to driver 506. The edge-detect receiver 200 can also be coupled to a second location of the medium where a propagated energy wave is detected. The edge-detect receiver in this embodiment is also in the feedback path. Similarly, the edge-detect receiver 200 initiates a pulsed energy wave being provided at the first location of the medium upon detecting a wave front of the propagated energy wave at the second location when the feedback path is closed.

Figure 6:
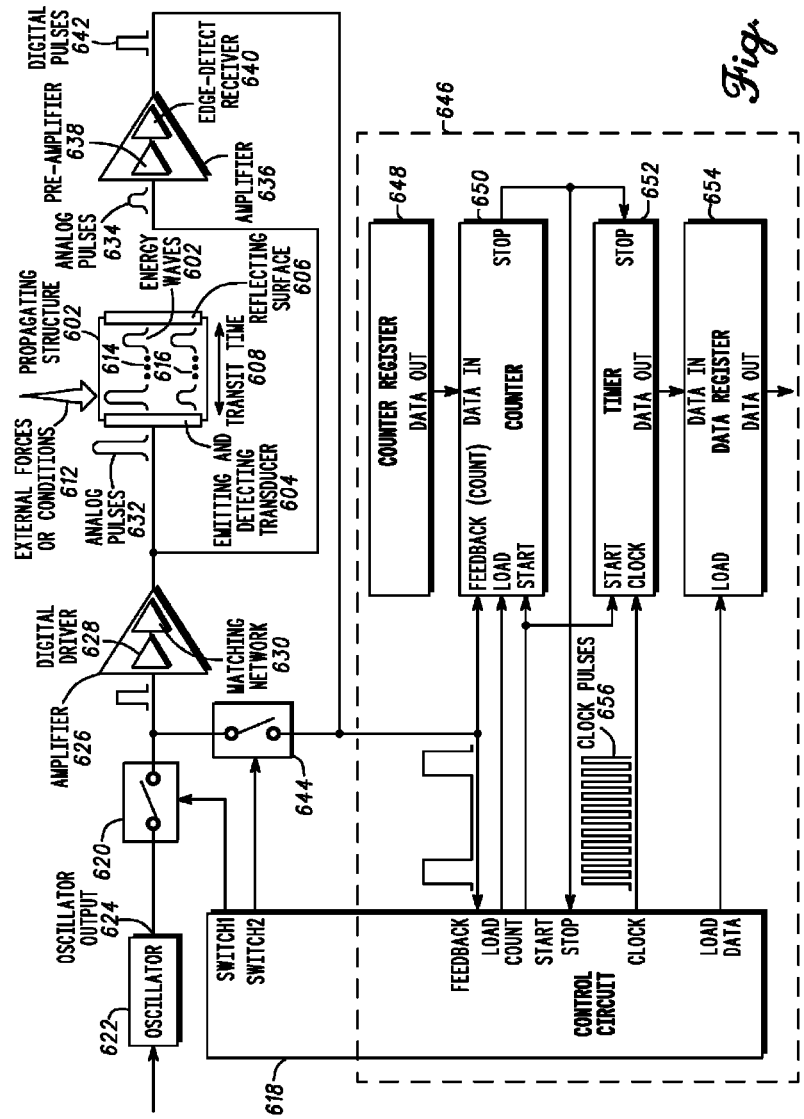
FIG. 6 is an exemplary block diagram of a propagation tuned oscillator (PTO) incorporating the edge-detect receiver circuit for operation in pulse echo mode.

FIG. 6 is an exemplary block diagram of a propagation tuned oscillator (PTO) incorporating the edge-detect receiver circuit 200 for operation in pulse echo mode. In particular, with respect to FIG. 4, it illustrates closed loop measurement of the transit time 412 of ultrasound waves 414 within the waveguide 408 by the operation of the propagation tuned oscillator 416. This example is for operation in a pulse echo mode. The system can also be operated in pulse mode and a continuous wave mode. Pulse mode does not use a reflected signal. Continuous wave mode uses a continuous signal. Briefly, the digital logic circuit 646 digitizes the frequency of operation of the propagation tuned oscillator.

In pulse-echo mode of operation a sensor comprising transducer 604, propagating structure 602, and reflecting surface 606 is used to measure the parameter. In general, the parameter to be measured affects the properties of the propagating medium. For example, an external force or condition 612 is applied to propagating structure 602 that changes the length of the waveguide in a path of a propagating energy wave. A change in length corresponds to a change in transit time of the propagating wave. Similarly, the length of propagating structure 602 corresponds to the applied force 612. A length reduction corresponds to a higher force being applied to the propagating structure 602. Conversely, a length increase corresponds to a lowering of the applied force 612 to the propagating structure 602. The length of propagating structure 602 is measured and is converted to force by way of a known length to force relationship.

Transducer 604 is both an emitting device and a receiving device in pulse-echo mode. The sensor for measuring a parameter comprises transducer 604 coupled to propagating structure 602 at a first location. A reflecting surface is coupled to propagating structure 602 at a second location. Transducer 604 has two modes of operation emitting and receiving. Transducer 604 emits an energy wave into the propagating structure 602 at the first location and subsequently generates a signal in a receiving mode corresponding to the reflected energy wave when it returns after being reflected.

A measurement sequence in pulse-echo mode is initiated when control circuitry 618 closes switch 620 coupling digital output 624 of oscillator 622 to the input of amplifier 626. One or more pulses provided to amplifier 626 initiates an action to propagate energy waves 610 having simple or complex waveforms through energy propagating structure or medium 602. Amplifier 626 comprises a digital driver 628 and matching network 630. In one embodiment, amplifier 626 transforms the digital output of oscillator 622 into pulses of electrical waves 632 having the same repetition rate as digital output 624 and sufficient amplitude to excite transducer 604.

Transducer 604 converts the pulses of electrical waves 632 into pulses of energy waves 610 of the same repetition rate and emits them into energy propagating structure or medium 602. The pulses of energy waves 610 propagate through energy propagating structure or medium 602 as shown by energy wave propagation 614 towards reflecting surface 606. Upon reaching reflecting surface 606, energy waves 610 are reflected by reflecting surface 606. Reflected energy waves propagate towards transducer 604 as shown by energy wave propagation 616. The reflected energy waves are detected by transducer 604 and converted into pulses of electrical waves 634 having the same repetition rate.

Amplifier 636 comprises a pre-amplifier 638 and edge-detect receiver 640. Amplifier 636 converts the pulses of electrical waves 634 into digital pulses 642 of sufficient duration to sustain the pulse behavior of the closed loop circuit. Control circuitry 618 responds to digital output pulses 642 from amplifier 636 by opening switch 620 and closing switch 644. Opening switch 620 decouples oscillator output 624 from the input of amplifier 626. Closing switch 644 creates a closed loop circuit coupling the output of amplifier 636 to the input of amplifier 626 and sustaining the emission, propagation, and detection of energy pulses through energy propagating structure or medium 602.

An equilibrium state is attained by maintaining unity gain around this closed loop circuit wherein electrical waves 632 input into transducer 604 and electrical waves 634 output by transducer 604 are in phase with a small but constant offset. Transducer 604 as disclosed above, outputs the electrical waves 634 upon detecting reflected energy waves reflected from reflecting surface 606. In the equilibrium state, an integer number of pulses of energy waves 610 propagate through energy propagating structure or medium 602.

Movement or changes in the physical properties of energy propagating structure or medium 602 change a transit time 608 of energy waves 610. The transit time 608 comprises the time for an energy wave to propagate from the first location to the second location of propagating structure 602 and the time for the reflected energy wave to propagate from the second location to the first location of propagating structure 602. Thus, the change in the physical property of propagating structure 602 results in a corresponding time period change of the energy waves 610 within energy propagating structure or medium 602. These changes in the time period of the repetition rate of the energy pulses 610 alter the equilibrium point of the closed loop circuit and repetition rate of operation of the closed loop circuit. The closed loop circuit adjusts such that electrical waves 632 and 634 correspond to the new equilibrium point. The repetition rate of energy waves 610 and changes to the repetition rate correlate to changes in the physical attributes of energy propagating structure or medium 602.

The physical changes may be imposed on energy propagating structure 602 by external forces or conditions 612 thus translating the levels and changes of the parameter or parameters of interest into signals that may be digitized for subsequent processing, storage, and display. Translation of the operating frequency into digital binary numbers facilitates communication, additional processing, storage, and display of information about the level and changes in physical parameters of interest. Similarly, the frequency of energy waves 610 during the operation of the closed loop circuit, and changes in this frequency, may be used to measure movement or changes in physical attributes of energy propagating structure or medium 602.

Prior to measurement of the frequency or operation of the propagation tuned oscillator, control logic 618 loads the loop count into digital counter 650 that is stored in count register 648. The first digital pulses 642 initiates closed loop operation within the propagation tuned oscillator and signals control circuit 618 to start measurement operations. At the start of closed loop operation, control logic 618 enables digital counter 650 and digital timer 652. In one embodiment, digital counter 650 decrements its value on the rising edge of each digital pulse output by edge-detect receiver 640. Digital timer 652 increments its value on each rising edge of clock pulses 656. When the number of digital pulses 642 has decremented, the value within digital counter 650 to zero a stop signal is output from digital counter 650. The stop signal disables digital timer 652 and triggers control circuit 618 to output a load command to data register 654. Data register 654 loads a binary number from digital timer 652 that is equal to the period of the energy waves or pulses times the value in counter 648 divided by clock period 656. With a constant clock period 656, the value in data register 654 is directly proportional to the aggregate period of the energy waves or pulses accumulated during the measurement operation. Duration of the measurement operation and the resolution of measurements may be adjusted by increasing or decreasing the value preset in the count register 648.

Figure 7:
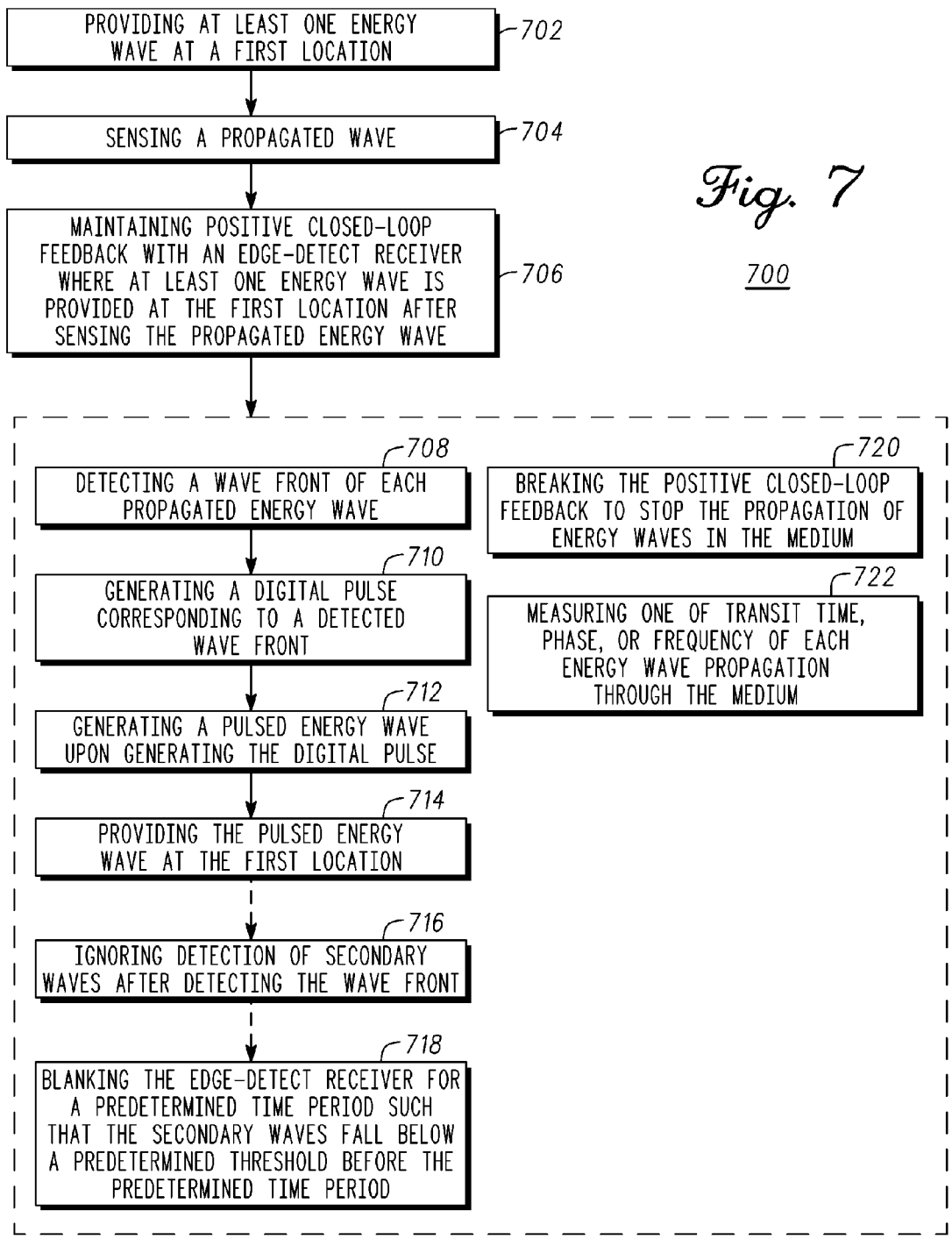
FIG. 7 is an exemplary method for measuring a parameter that corresponds to a transit time of an energy wave propagating through a medium in accordance with the present invention.

FIG. 7 is an exemplary method 700 for measuring a parameter that corresponds to a transit time of an energy wave propagating through a medium in accordance with the present invention. The method can be practiced with more or less than the number of steps shown and is not limited to the order shown. In a step 702, one or more pulsed energy waves are provided to a medium. The energy waves are provided at a first location on the medium. In general, the medium is subjected to the parameter being measured. In a non-limiting example, the parameter is a force or pressure that changes the medium dimensionally. The emitted pulsed energy waves propagate through the medium. In one embodiment, the medium is a waveguide that directs the propagation. In a step 704, each energy wave is sensed or detected. In a pulse mode, the energy wave propagates to a second location on the medium where it is sensed. The second location in pulse mode is different from the first location. In a pulse-echo mode, an energy wave is reflected upon propagating to the second location. The reflected wave is sensed or detected upon returning to the first location. Thus, the second location in step 704 corresponds to the first location on the medium in a pulse echo mode application. In a step 706, a positive closed loop feedback is maintained. An edge-detect receiver as disclosed herein is in the feedback path of the closed loop. A pulsed energy wave is emitted or provided at the first location of the medium upon sensing or detecting an energy wave that has propagated through the medium thereby continuing the process of propagating energy waves, sensing energy waves, and emitting energy waves in the medium.

In a step 708, a wave front of each energy wave is sensed or detected. In pulse echo mode, an energy wave propagates through the medium and is reflected. In one embodiment, the wave front of the reflected energy wave is sensed at the first location where it was initially emitted. In an example where the energy wave comprises ultrasonic acoustic waves, sensing includes the conversion of the acoustic waves to corresponding electrical waves.

In a step 710, a digital pulse that corresponds to a sensed energy wave is output. The digital pulse is generated by the edge-detect receiver upon detecting the wave front of the energy wave. In the example, the leading edge of the electrical waves corresponding to the energy waves is sensed that triggers the generation of the digital pulse.

In a step 712, an energy wave is generated by or triggered from the digital pulse of step 710. In a step 714, the energy wave is emitted at the first location of the medium. The energy wave propagates from the first location towards the reflective surface at the second location of the medium thus continuing the propagation of energy waves in the medium.

In a step 716, secondary waves of an energy wave are ignored. In general, an energy wave comprises secondary waves that would initiate subsequent digital pulse generation in step 710 and subsequent emission of unwanted energy waves into the medium. The edge-detect receiver suppresses the generation of these unwanted energy waves by preventing the generation of digital pulses due to the secondary waves after the wave front has been sensed.

In a step 718, the edge-detect receiver is blanked for a predetermined period of time. The blanking process occurs after the wave front is sensed and prevents the edge-detect from reacting to the secondary waves (e.g. ignoring) of the energy wave. In general, an energy wave emitted into the medium is a damped waveform that typically comprises more than one voltage or current transition that would trigger the generation of digital pulses. In one embodiment, the signal level of the electrical waves corresponding to the sensed energy waves has to be above a predetermined threshold to generate a digital pulse in step 710. Secondary waves having a signal magnitude below the predetermined threshold will not generate the digital pulse. In a non-limiting example, the secondary waves of an energy wave comprise a damped form such that the magnitude naturally decays below the predetermined threshold. In one embodiment, the magnitude of the secondary waves fall below the predetermined threshold before the predetermined time. The blanking process is turned off after the predetermined time. Thus, the edge-detect receiver is blanked for a time during which the secondary waves could trigger the generation of digital pulses and enabled after the predetermined time.

In a step 720, the positive closed-loop feedback is broken to stop the propagation of pulsed energy waves in the medium. In one embodiment, the digital pulse generated in step 710 from the sensing of the wave front of an energy wave is prevented from triggering the generation of a new energy wave thereby opening the loop.

In a step 722, one of transit time, phase, or frequency of the energy waves propagating through the medium is measured. As mentioned previously, the parameter being measured affects the medium. The change in the medium due to the parameter affects transit time, phase, or frequency. Furthermore, the parameter has a known relationship with the medium. Thus, the measurement of the transit time, phase, or frequency can be related back to the parameter. A conversion is performed to produce an accurate measurement of the parameter using energy wave propagation.

The present invention is applicable to a wide range of medical and nonmedical applications including, but not limited to, frequency compensation; control of, or alarms for, physical systems; or monitoring or measuring physical parameters of interest. The level of accuracy and repeatability attainable in a highly compact sensing module or device may be applicable to many medical applications monitoring or measuring physiological parameters throughout the human body including, not limited to, bone density, movement, viscosity, and pressure of various fluids, localized temperature, etc. with applications in the vascular, lymph, respiratory, digestive system, muscles, bones, and joints, other soft tissue areas, and interstitial fluids.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. A sensor for measuring a parameter of the muscular-skeletal system where the parameter being measured affects a medium, where the medium is coupled to or part of the muscular-skeletal system, where the medium is configured to receive at least one pulsed energy wave that traverses the medium, where a time, frequency, or phase is measured of the at least one pulsed energy wave and converted to the parameter and where the sensor comprises:

an edge detect circuit configured to detect a pulsed energy wave that has traversed the medium where the edge detect circuit comprises:
 a differentiator configured to receive a pulsed energy wave signal that corresponds to the pulsed energy wave that has traversed the medium where the differentiator is configured to detect a change in slope;
 a pulse circuit coupled to the differentiator configured to generate a pulse upon detecting a leading edge of the pulsed energy wave signal; and
 a deblank circuit coupled to the pulse circuit where the deblank circuit is configured to support desensitizing the edge detect circuit to trailing signals of the pulsed energy wave signal after the leading edge of the pulsed energy wave signal is detected.

2. The sensor of claim 1 further including a first transducer where the first transducer is configured to couple to the medium at a first point and where the first transducer is configured to transmit pulsed energy waves into the medium.

3. The sensor of claim 2 further including a second transducer where the second transducer is configured to couple to the medium at a second point and where the second transducer couples to the edge detect circuit.

4. The sensor claim 3 where the second transducer is configured to receive pulsed energy waves from the medium and where the second transducer is configured to output the pulsed energy wave signal corresponding to a received pulsed energy wave.

5. The sensor or claim 2 further including a reflective surface where the reflective surface is configured to couple to the medium at a second point.

6. The sensor of claim 5 where the reflective surface is configured to reflect pulsed energy waves back to the first point of the medium, where the first transducer is configured to receive pulsed energy waves, where the first transducer couples to the edge detect circuit, and where the first transducer is configured to output the pulsed energy wave signal corresponding to a received pulsed energy wave.

7. The sensor of claim 1 further including a preamplifier coupled to the differentiator where the preamplifier is configured to receive and amplify the pulsed energy wave signal.

8. The sensor of claim 7 where the deblank circuit couples to the preamplifier and where the deblank circuit initiates one of gain reduction of the preamplifier, decoupling of an input of the preamplifier from receiving the pulsed energy wave signal, changing the frequency response of the preamplifier, or disabling the preamplifier for a predetermined time whereby the edge detect circuit is desensitized from responding to trailing portions of the pulsed energy wave signal.

9. The sensor of claim 1 where the change in slope detected by the differentiator comprises a change in current.

10. The sensor of claim 9 where the change in current corresponds to detection of the leading edge of the pulsed energy wave.

11. A sensor for measuring a parameter of the muscular-skeletal system where the parameter being measured affects a medium, where the medium is coupled to or part of the muscular-skeletal system, where the medium is configured to receive at least one pulsed energy wave that traverses the medium, where a time, frequency, or phase is measured of the at least one pulsed energy wave and converted to the parameter and where the sensor comprises:

a transducer coupled to the medium at a first point; and
an edge detect circuit configured to detect a pulsed energy wave that has traversed the medium where the edge detect circuit comprises:
  a differentiator configured to receive a pulsed energy wave signal that corresponds to the pulsed energy wave that has traversed the medium where the differentiator detects a change in slope of the pulsed energy wave signal;
  a pulse circuit coupled to the differentiator configured to generate a pulse on detecting a leading edge of the pulsed energy wave; and
  a deblank circuit coupled to the pulse circuit where the deblank circuit is configured to support desensitizing the edge detect circuit to trailing signals of the pulsed energy wave signal after the leading edge of the pulsed energy wave signal is detected.

12. The sensor of claim 11 further including a second transducer at a second point of the medium where the transducer is configured to transmit pulsed energy waves into the medium, where the second transducer couples to the edge detect circuit, and where the second transducer is configured to generate the pulsed energy wave signal corresponding to the pulsed energy wave.

13. The sensor claim 11 where a reflective surface is coupled to the medium at a second point, where the reflective surface is configured to reflect pulsed energy waves back to the first point of the medium, where the transducer is configured to receive pulsed energy waves, and where the first transducer is configured to output the pulsed energy wave signal corresponding to a received pulsed energy wave.

14. The sensor of claim 11 further including a preamplifier coupled to the differentiator where the preamplifier is configured to receive and amplify the pulsed energy wave signal and where the deblank circuit is configured to blank the preamplifier from amplifying a remaining portion of the pulsed energy wave signal when the leading edge of the pulsed energy wave is detected.

15. The sensor of claim 11 further including a preamplifier coupled to the differentiator where the deblank circuit couples to the preamplifier and where the deblank circuit initiates one of gain reduction of the preamplifier, decoupling of an input of the preamplifier from receiving the pulsed energy wave signal, changing the frequency response of the preamplifier, or disabling the preamplifier for a predetermined time.

16. A sensor for measuring a parameter of the muscular-skeletal system where the parameter being measured affects a medium, where the medium is coupled to or part of the muscular-skeletal system, where the medium is configured to receive at least one pulsed energy wave that traverses the medium, where a time, frequency, or phase is measured of the at least one pulsed energy wave and converted to the parameter and where the sensor comprises:

an edge detect circuit configured to detect a pulsed energy wave that has traversed the medium where the edge detect circuit comprises:
  a preamplifier configured to receive a pulsed energy wave signal that corresponds to the pulsed energy wave where the preamplifier is configured to receive and amplify the pulsed energy wave signal;
  a differentiator coupled to the preamplifier where the differentiator is configured to receive the pulsed energy wave signal to detect a change in slope;
  a pulse circuit coupled to the differentiator configured to generate a pulse on detecting a leading edge of the pulsed energy wave; and
  a deblank circuit coupled to the preamplifier where the deblank circuit is configured to blank the preamplifier from amplifying a remaining portion of the pulsed energy wave signal after the leading edge of the pulsed energy wave is detected.

17. The sensor of claim 16 further including:
a first transducer coupled to a first point of the medium where the first transducer is configured to transmit pulsed energy waves into the medium;
a second transducer coupled to a second point of the medium where the second transducer is configured to receive pulsed energy waves from the medium, where the second transducer couples to the edge detect circuit, and where the second transducer is configured to generate the pulsed energy wave signal corresponding to received pulsed energy waves.

18. The sensor claim 16 further including:
a first transducer coupled to a first point of the medium where the first transducer is configured to transmit pulsed energy waves into the medium;
a reflective surface coupled to the medium at a second point, where the reflective surface is configured to reflect pulsed energy waves back to the first point of the medium, where the first transducer is coupled to the edge detect circuit, where the first transducer is configured to receive pulsed energy waves, and where the first transducer is configured to output the pulsed energy wave signal corresponding to a received pulsed energy wave.

19. The sensor of claim 16 where the change in slope detected by the differentiator comprises a change in current.

20. The sensor of claim 19 where the change in current corresponds to detection of the leading edge of the pulsed energy wave.

* * * * *